United States Patent
Aznar et al.

(10) Patent No.: US 7,448,272 B2
(45) Date of Patent: Nov. 11, 2008

(54) SYSTEM AND METHOD FOR INSPECTING SPOT WELD

(75) Inventors: Daniel Ruiz Aznar, Valencia (ES); Juan Martinez Collado, Valencia (ES); Manuel Suarez Jorda, Valencia (ES); Maria Alonso Ortiz, Valencia (ES); Jose Luis Perez Guerrero, Valencia (ES); Jesus Belda Pla, Valencia (ES)

(73) Assignees: Ford Global Technologies, LLC, Dearborn, MI (US); Eines S.C.V., Valencia (ES)

( * ) Notice: Subject to any disclaimer, the term of this patent is extended or adjusted under 35 U.S.C. 154(b) by 404 days.

(21) Appl. No.: 11/275,317

(22) Filed: Dec. 22, 2005

(65) Prior Publication Data

US 2007/0144262 A1    Jun. 28, 2007

(51) Int. Cl.
*G01N 29/26* (2006.01)
*G01N 29/06* (2006.01)

(52) U.S. Cl. ...................................................... 73/634
(58) Field of Classification Search .................... 73/634
See application file for complete search history.

(56) References Cited

U.S. PATENT DOCUMENTS

| | | | | |
|---|---|---|---|---|
| 4,204,434 A | * | 5/1980 | Whitsel | 73/622 |
| 4,208,917 A | | 6/1980 | Aoyama et al. | |
| 5,537,875 A | * | 7/1996 | Viehmann et al. | 73/588 |
| 6,072,144 A | | 6/2000 | Perrymann | |
| 6,250,163 B1 | | 6/2001 | MacLauchlan et al. | |
| 6,414,260 B1 | | 7/2002 | Vogt | |
| 6,414,261 B1 | | 7/2002 | Maetschke | |
| 6,585,146 B2 | | 7/2003 | Shepard | |
| 7,132,617 B2 | * | 11/2006 | Lee et al. | 219/109 |
| 7,210,329 B2 | * | 5/2007 | Buschke et al. | 73/1.82 |
| 2003/0234239 A1 | | 12/2003 | Lee et al. | |
| 2004/0245315 A1 | | 12/2004 | Maev et al. | |
| 2006/0109002 A1 | * | 5/2006 | Buschke et al. | 324/237 |

FOREIGN PATENT DOCUMENTS

| | | | |
|---|---|---|---|
| DE | 101 25 782 A1 | * | 3/2003 |
| DE | 102 22 600 A1 | * | 12/2003 |
| EP | 0 833 151 A2 | * | 4/1998 |
| GB | 1415389 | | 11/1975 |
| JP | 61223648 A | * | 10/1986 |
| JP | 2000146928 A | * | 5/2000 |
| WO | WO 2004/005913 A1 | * | 1/2004 |
| WO | WO 2004/036144 A2 | * | 4/2004 |

OTHER PUBLICATIONS

Spot Weld Testing, Application Note: 930-145, Olympus NDT (Copyright 2005).

* cited by examiner

*Primary Examiner*—Hezron E. Williams
*Assistant Examiner*—Rose M Miller
(74) *Attorney, Agent, or Firm*—Raymond L. Coppiellie; Brooks Kushman P.C.

(57) ABSTRACT

A system and method for inspecting a spot weld on a workpiece. The system may include an actuator, an inspection assembly coupled to the actuator, and a controller electronically coupled to the inspection assembly. The inspection assembly may include an ultrasound device and one or more adjustment motors coupled to the ultrasound device.

20 Claims, 5 Drawing Sheets

SYSTEM AND METHOD FOR INSPECTING SPOT WELD

BACKGROUND OF THE INVENTION

1. Field of the Invention

The invention relates generally to a system and method for inspecting a spot weld, and more particularly to a system and method for using an ultrasound device to inspect a spot weld.

2. Background Art

Presently, spot weld inspection is performed using a hand held test device. Such manual inspection generally provides a high degree of flexibility in the positioning of the test device relative to the spot weld. However, manual inspection requires a substantial amount of time such that on-line inspection (i.e., inspection performed without removing a workpiece from the normal build sequence) may not be feasible. Similarly, the substantial amount of time require to perform a manual inspection may prohibit a 100% inspection rate (i.e., inspection may be limited to a representative sample of workpieces). Last, manual inspection may expose the spot weld and/or workpiece to an increased risk of damage due to increased part handling and human error.

SUMMARY OF THE INVENTION

The present invention generally provides a system and method for inspecting a spot weld that may eliminate or reduce one or more deficiency associated with conventional inspection of spot welds. Accordingly, one or more embodiments of the present invention may decrease the amount of time required to inspect a spot weld such that on-line inspection and/or an increase in the inspection rate may be provided. In addition, one or more embodiments of the present invention may reduce the risk of damaging the spot weld and/or part during inspection.

In at least one embodiment of the present invention, a system for inspecting a spot weld on a workpiece is provided. The system comprises an actuator, an inspection assembly coupled to the actuator, and a controller electronically coupled to the inspection assembly. The actuator is configured to position the inspection assembly at an initial inspection position. The inspection assembly comprises an ultrasound device and one or more adjustment motors coupled to the ultrasound device. The ultrasound device is configured to generate one or more ultrasound waves and receive one or more echo waves. The controller is configured to identify a spot weld echo state based at least in part on the one or more echo waves, and determine whether the spot weld echo state corresponds to a member of a set of predetermined echo states. The one or more adjustment motors are configured to manipulate the ultrasound device when the spot weld echo state does not correspond to a member of the set of predetermined echo states.

In at least one other embodiment of the present invention, a method for inspecting a spot weld on a workpiece is provided. The method comprises the steps of moving an inspection assembly comprising an ultrasound device to an initial inspection position proximate the spot weld, generating one or more ultrasound waves using the ultrasound device, receiving one or more echo waves using the ultrasound device, identifying, using a controller, a spot weld echo state based at least in part on the one or more echo waves, determining whether the spot weld echo state corresponds to a member of a set of predetermined echo states, and manipulating the ultrasound device when the spot weld echo state does not correspond to a member of the set of predetermined echo states.

In yet at least one other embodiment of the present invention, a system for inspecting a spot weld on a workpiece is provided. The system comprises an actuator, an inspection assembly coupled to the actuator, and one or more controllers electronically coupled to at least one of the actuator and the inspection assembly. The inspection assembly comprises an ultrasound device and one or more adjustment motors coupled to the ultrasound device. The one or more controllers are configured to perform the steps of moving the ultrasound device via at least one of the actuator and the one or more adjustment motors to an initial inspection position proximate the spot weld, generating one or more ultrasound waves via the ultrasound device, receiving one or more echo waves via the ultrasound device, identifying a spot weld echo state based at least in part on the one or more echo waves, determining whether the spot weld echo state corresponds to a member of a set of predetermined echo states, manipulating the ultrasound device via the one or more adjustment motors when the spot weld echo state does not correspond to a member of the set of predetermined echo states, and generating an accept signal or a reject signal based at least in part on the spot weld echo state when the spot weld echo state corresponds to a member of the set of predetermined echo states.

DETAILED DESCRIPTION

Figure 1:
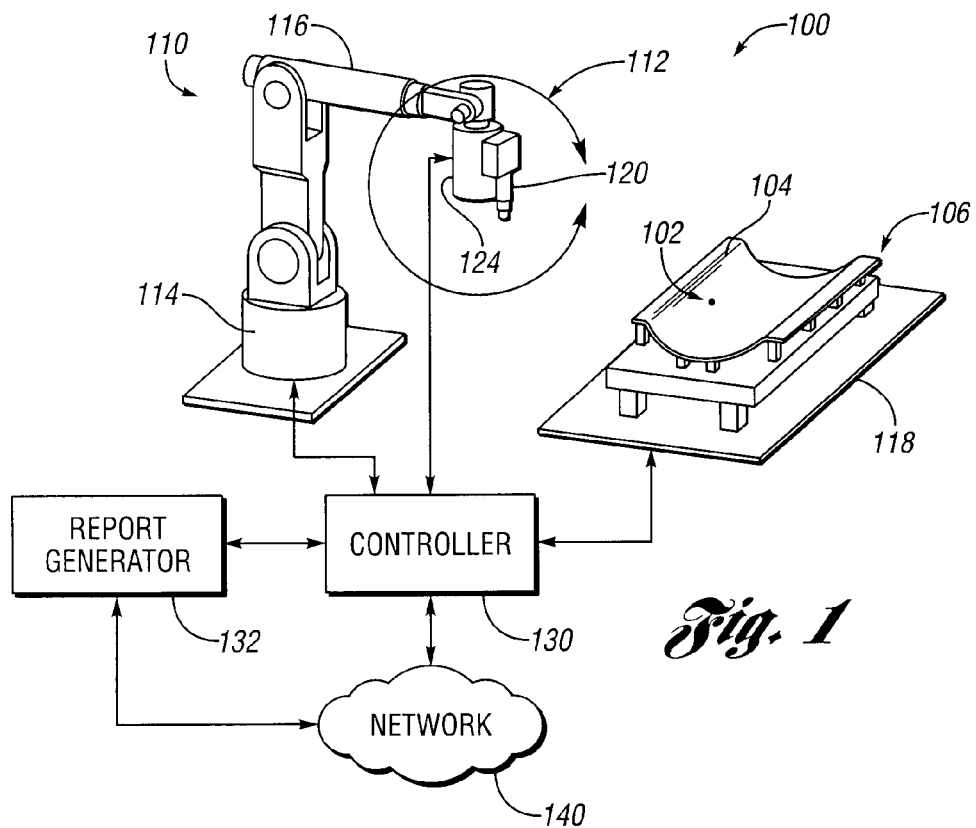
FIG. 1 is a diagram of a system for inspecting a spot weld according to an embodiment of the present invention.

Referring to FIG. 1, a diagram is provided of a system 100 for inspecting a spot weld 102 according to an embodiment of the present invention. The system 100 may comprise a workpiece 104 having one or more spot welds 102, a workpiece presenter 106, an actuator 110, an inspection assembly 112, and/or a controller 130. In at least one embodiment, the system 100 may be implemented in connection with a material handling system 118, such as a vehicle assembly line, an automotive assembly line, and/or the like, for inspecting the one or more spot welds 102 on the workpiece 104.

The workpiece presenter 106 may be of any suitable type, such as a fixture adapted to hold (i.e., couple to) the workpiece 104 in a predetermined position. The workpiece presenter 106 may be stationary or may be integrated with (i.e., coupled to) a material handling system 118 (e.g., assembly line) that moves the workpiece presenter 106 between a plurality of work cells. In general, the workpiece presenter 106 may present the workpiece 104 to the inspection assembly 112 for inspection of one or more spot welds 102.

The actuator 110 may be of any suitable configuration. In the embodiment shown in FIG. 1, the actuator 110 is configured as a multi-axis robot having a base 114 and an articulating arm 116. However, the actuator 110 may be of any suitable type and may have any suitable number of movement axes and/or degrees of freedom to meet the design criteria of a particular application.

The inspection assembly 112 may couple to the actuator 110 and generally includes an ultrasound inspection unit 120. The ultrasound inspection unit 120 may be configured to generate one or more ultrasound waves and/or receive one or more echo waves. In the embodiment shown in FIG. 1, the actuator 110 is a multi-axis robot and the inspection assembly 112 is coupled to the articulating arm 116 of the robot as an end effector. However, the inspection assembly 112 may couple by any appropriate mechanism to any appropriate type of actuator 110 to meet the design criteria of a particular application.

The actuator 110 may be configured to position the inspection assembly 112 at (i.e., to) an initial inspection position. In at least one embodiment, the initial inspection position may be proximate the spot weld 102. When the workpiece presenter 106 is integrated with a material handling system 118, the actuator 110 may be further configured to move the inspection assembly 112 during inspection of the spot weld 102 such that a relative position between the inspection assembly 112 and the spot weld 102 is substantially (i.e., within a predetermined tolerance) constant while the workpiece presenter 106 moves via the material handling system 118 (e.g., while the workpiece presenter 106 moves along an assembly line).

Optionally, the system 100 may further include an artificial vision device 124 configured to obtain image data corresponding to the spot weld 102. The initial inspection position and/or relative position may be determined/maintained, respectively, based at least in part on the image data. In the embodiment shown in FIG. 1, the inspection assembly 112 comprises the artificial vision device 124. However, the artificial vision device 124 may be mounted at any appropriate location to meet the design criteria of a particular application.

The system 100 may include a controller 130 for controlling the functionality of one or more components (e.g. 110, 112, 118, 120, 124, and/or the like) of the system 100. In general, the controller 130 may be a computer or other logical device such as a programmable logic controller (i.e., PLC) which executes programs and/or which performs other logical exercises. It is contemplated that control of the functionality of the one or more components of the system 100 may be incorporated into a single controller, such as is shown in FIG. 1. Alternatively, control of the functionality may be distributed among a plurality of controllers, such as a material handling controller, an inspection assembly controller including an ultrasound device controller and/or an artificial vision device controller, an actuator controller, and/or the like. In general, controller inputs and outputs may be received and passed between controllers 130 via a controller network (not shown), dedicated communication wires (not shown), and/or the like.

In at least one embodiment, the controller 130 may be electronically coupled to the inspection assembly 112 and configured to identify a spot weld echo state based at least in part on the one or more echo waves, determine when the spot weld echo state corresponds to a member of a set of predetermined echo states, and generate an accept signal or a reject signal based at least in part on the spot weld echo state when the spot weld echo state corresponds to a member of the set of predetermined echo states.

Furthermore, one or more embodiments may include a report generator 132 electronically coupled to (e.g., integrated with, coupled via a network to, etc.) the controller 130. The report generator 132 may be configured to receive inspection data based at least in part on the spot weld echo state and generate a report based at least in part on the inspection data. In addition or alternatively, the report generator 132 may be configured to store (i.e., archive) the inspection data for subsequent retrieval.

As illustrated in FIG. 1, the controller 130 and/or the report generator 132 may be electronically coupled to a network 140 (e.g., a local area network, a wide area network, the Internet, and/or the like) for providing/receiving information and/or data to/from a remote user (not shown).

Figure 2:
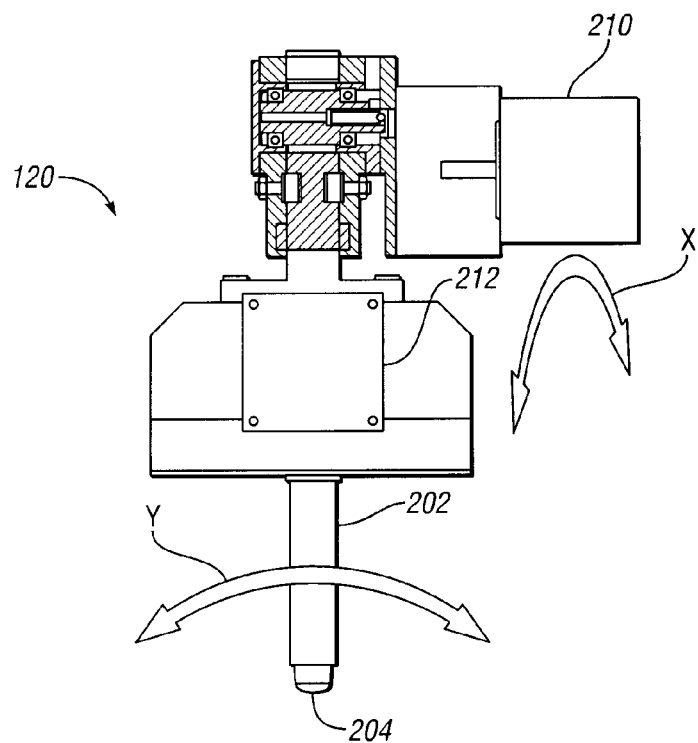
FIG. 2 is a diagram of an ultrasound inspection unit according to an embodiment of the present invention.

Referring to FIG. 2, a diagram is provided of the ultrasound inspection unit 120 according to an embodiment of the present invention. As illustrated, the ultrasound inspection unit 120 may comprise an ultrasound device 202, and one or more adjustment motors (e.g., 210, 212) coupled to the ultrasound device 202.

The ultrasound device 202 may be configured to generate one or more ultrasound waves and/or receive one or more echo waves. Furthermore, the ultrasound device 202 may include a rubber tip 204 (e.g., a hard rubber tip) for coupling the ultrasound device 202 to the spot weld 102 such that ultrasound waves may be propagated/received to/from the workpiece 104, respectively. In at least one embodiment, use of the rubber tip 204 may reduce the risk of damaging the workpiece 104, the spot weld 202, and/or the ultrasound device 202 during inspection of the spot weld 102.

The one or more adjustment motors (e.g., 210, 212) may be configured to manipulate (i.e., move, position, etc.) the ultrasound device 202. In at least one embodiment, the adjustment motors may be configured to move the ultrasound device 202 to an initial inspection position such as a position proximate the spot weld 102. In at least one other embodiment, the adjustment motors may be configured to manipulate the ultrasound device 202 when the spot weld echo state does not correspond to a member of the set of predetermined echo states. For example, a first adjustment motor (e.g., a stepper motor) 210 may be configured to manipulate the ultrasound device 202 about an X-axis and a second adjustment motor 212 may be configured to manipulate the ultrasound device 202 about a Y-axis. Accordingly, the first 210 and second 212 adjustment motors may cooperate to position the ultrasound device 202 in space.

Figure 3A:
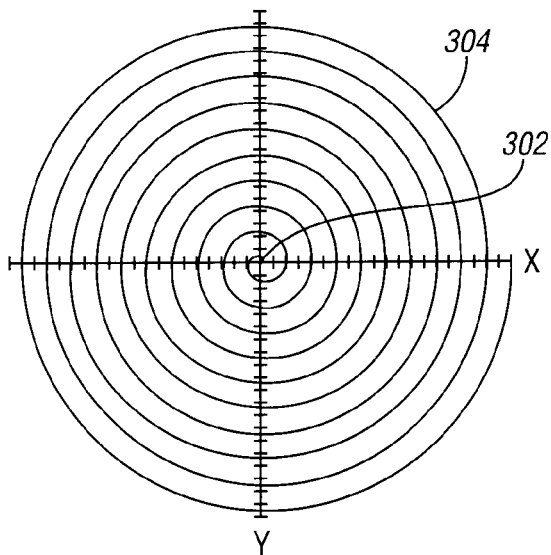
FIGS. 3(a-c) are plots illustrating manipulation of the ultrasound device according to various embodiments of the present invention.

As illustrated in FIG. 3a, the one or more adjustment motors (e.g., 210, 212) may manipulate the ultrasound device 202 such that an end of the ultrasound device 202 proximate the workpiece 104 is held substantially stationary in space, such as at point 302, while an end of the ultrasound device 202 proximate the actuator 110 is manipulated to follow a spiral 304 radiating outward from the point 302.

Figure 3B:
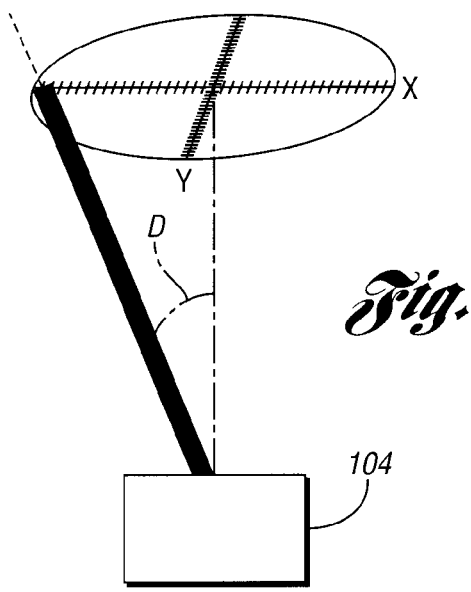

As illustrated in FIG. 3b, the manipulation illustrated in FIG. 3a generally provides inclination (i.e., slant, deviation from vertical) of the ultrasound device 202 in relation to the spot weld 102. In at least one embodiment, the maximum degree of inclination (i.e., D) may be 10 degrees. However, the maximum degree of inclination may be any appropriate value to meet the design criteria of a particular application.

Figure 3C:
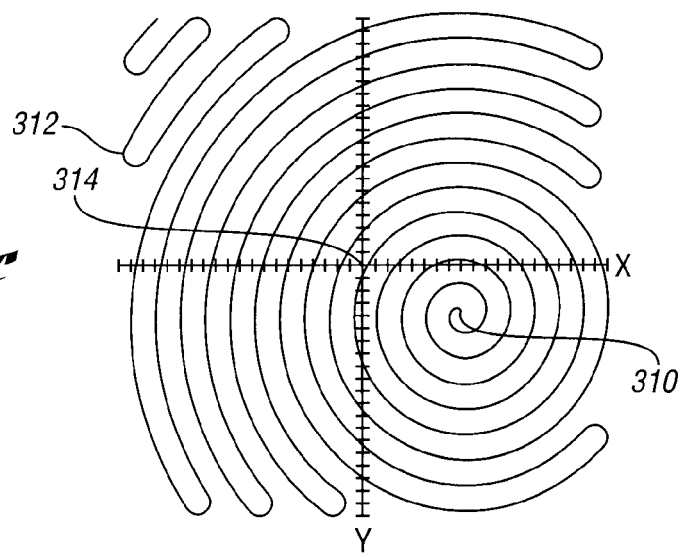

As illustrated in FIG. 3c, the ultrasound device 202 may be optionally manipulated via the one or more adjustment motors (e.g., 210, 212) such that an end of the ultrasound device 202 proximate the workpiece 104 is held substantially stationary in space, such as at point 310, while an end of the ultrasound device 202 proximate the actuator 110 is manipulated to follow the curve 312 radiating outward from the point 310. In at least one embodiment, the curve 312 may be advantageously implemented to provide inspection over an operational range of the adjustment motors (e.g., 210, 212) when the position of the spot weld 102 is not aligned with the spatial origin 314 of the ultrasound inspection unit 112.

Figure 4:
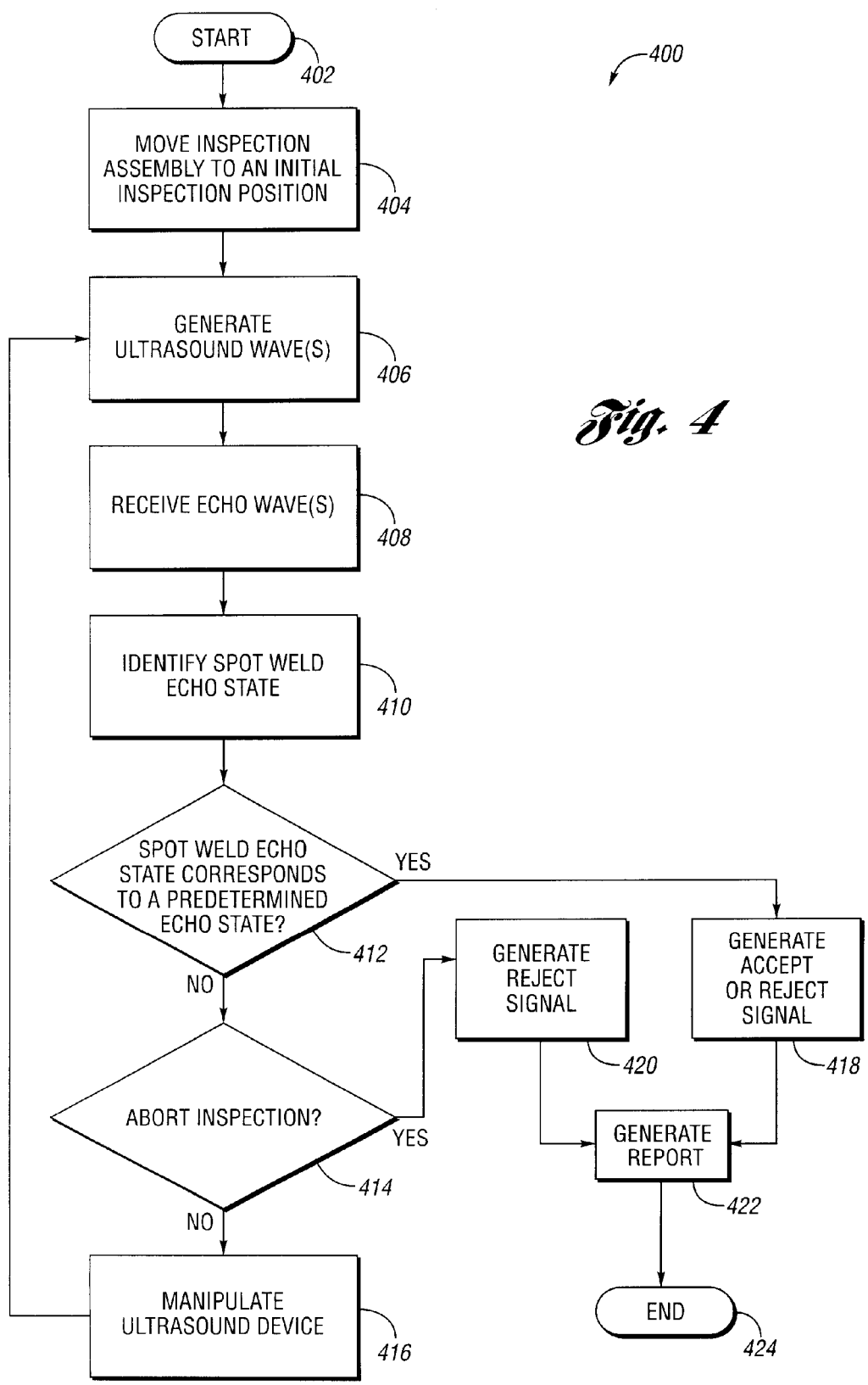
FIG. 4 is a flow diagram of a method for inspecting a spot weld on a workpiece according to an embodiment of the present invention.

Referring to FIG. 4, a flow diagram of a method 400 for inspecting a spot weld (e.g., 102) on a workpiece (e.g., 104) according to at least one embodiment of the present invention is shown. The method 400 may be advantageously implemented in connection with the system 100, described previously in connection with FIGS. 1 and 2, and/or any appropriate system to meet the design criteria of a particular application. In particular the method 400 is generally performed by a logical device, such as the controller 130. The method 400 generally includes a plurality of blocks or steps that may be performed serially. As will be appreciated by one of ordinary skill in the art, the order of the blocks/steps shown in FIG. 4 are exemplary and the order of one or more block/step may be modified within the spirit and scope of the present invention. Additionally, the blocks/steps of the method 400 may be performed in at least one non-serial (or non-sequential) order, and one or more blocks/steps may be omitted to meet the design criteria of a particular application. Similarly, two or more of the blocks/steps of the method 400 may be performed in parallel. Step 402 generally represents an entry point into the method 400.

At step 404 an inspection assembly (e.g., 112) is generally moved to (i.e., positioned at) an initial inspection position. In at least one embodiment, the inspection assembly may be moved to the initial inspection position using an actuator (e.g., 110). The initial inspection position is generally proximate a spot weld (e.g., 102) and may be defined such that an ultrasound device (e.g., 202) coupled to the inspection assembly is substantially perpendicular to and/or substantially centered on the spot weld when the inspection assembly is at the initial inspection position.

At step 406, one or more ultrasound waves may be generated using the ultrasound device.

At step 408, one or more echo waves (i.e., an ultrasound wave reflected by an object) may be received using the ultrasound device.

At step 410, a spot weld echo state may be identified using a controller (e.g., 130). The spot weld echo state is generally based at least in part on the one or more echo waves and may, in at least one embodiment, be graphically displayed (i.e., represented) on a graphical user interface (not shown) as illustrated in connection with FIGS. 6(a-c). Furthermore, as discussed in connection with FIGS. 6(a-c), the time period between (i.e., frequency of) sequential primary echo waves (i.e., waves corresponding to welded portions of the workpiece) is generally proportional to the thickness of the spot weld. Similarly, spot weld diameter generally corresponds to the presence/absence of secondary echo waves (i.e., waves corresponding to non-welded portions of the workpiece). In general, primary echo waves may exhibit greater wave amplitudes than secondary echo waves. Accordingly, in one embodiment, primary echo waves may be distinguished from secondary echo waves based at least in part on wave amplitude.

At decision block 412, a controller and/or other logical device generally determines whether (i.e., when) the spot weld echo state corresponds to a member of a set of predetermined echo states. In at least one embodiment, the set of predetermined echo states comprises known good spot weld echo states (i.e., echo wave patterns that have been determined to correspond to a good spot weld). In at least one other embodiment, the set of predetermined echo states comprises known bad spot weld echo states (i.e., echo wave patterns that have been determined to correspond to an undesirable spot weld). In yet another embodiment, the set of predetermined echo states includes both known good and known bad spot weld echo states. However, any appropriate echo state may be included in the set of predetermined echo states to meet the design criteria of a particular application. The method 400 generally proceeds to step 418 when the spot weld echo state corresponds to a member of the set of predetermined echo states (i.e., the YES leg of decision block 412). Otherwise, the method 400 may fall through to decision block 414 (i.e., the NO leg of decision block 412).

At decision block 414, a controller and/or other logical device may determine whether to abort inspection of the spot weld (i.e., abort method 400). Any of a number of actions or occurrences may be implemented to trigger the controller and/or other logical device to abort the inspection of the spot weld. In one example, the inspection may be aborted when the method 400 has been performed for a predetermined amount of time (i.e., a timeout occurs). In another example, the inspection may be aborted when the method 400 has performed decision block 414 a predetermined number of times (i.e., maximum number of cycles performed). However, the controller and/or other logical device may determine whether to abort inspection of the spot weld based on any appropriate stimulus to meet the design criteria of a particular application. The method 400 generally proceeds to step 420 when inspection is aborted (i.e., the YES leg of decision block 414). Otherwise, the method 400 may fall through to decision block 416 (i.e., the NO leg of decision block 414).

At step 416, the ultrasound device may be manipulated. In one embodiment, the step of manipulating the ultrasound device comprises the step of holding a first end of the ultrasound device adjacent the spot weld substantially fixed in space while moving a second end of the ultrasound device opposite the first end along a path substantially defined by a spiral such that an increasing angle is formed between the ultrasound device and an axis passing through the first and second ends prior to the manipulation (i.e. the angle increases as the second end moves outward along the path substantially defined by the spiral). In at least one embodiment, the increasing angle may have a maximum value of 10 degrees (i.e., the angle may stop increasing when the angle equals 10 degrees). However, the maximum value may be any appropriate value to meet the design criteria of a particular application. In general, one or more adjustment motors (e.g., 210, 212) and/or other adjustment devices may be implemented to manipulate the ultrasound device. From step 416, the method 400 generally returns to step 406. In at least one embodiment, step 406, step 408, step 410, decision block 412 and/or decision block 414 may be performed after the ultrasound device is manipulated. In at least one other embodiment, step 406, step 408, step 410, decision block 412 and/or decision block 414 may be performed concurrently with step 416 (i.e., while the ultrasound device is manipulated).

At step 418, a controller and/or other logical device may generate an accept or reject signal based at least in part on the spot weld echo state when the spot weld echo state corresponds to a member of the set of predetermined echo states. From step 418, the method 400 may fall through to step 422.

At step 420, a controller and/or other logical device may generate a reject signal when inspection of the spot weld is aborted. From step 420, the method 400 may fall through to step 422.

At step 422, a report may be generated using a controller and/or other logical device (e.g., 132). In at least one embodiment, the report may be based at least in part on the spot weld echo state of one or more spot welds. In general, the report may be stored on any appropriate medium and/or device, such as paper, magnetic disk, optical disk, solid state device, solid state memory, and/or the like. Similarly, historical data corresponding to inspection of one or more spot welds may be stored on any appropriate medium and/or device by the controller and/or other logical device. It should be understood that the step of generating a report may include modifying an existing report in addition to and/or in place of creating an entirely new report. From step 422, the method 400 may fall through to step 424.

Step 424 generally represents an exit point out of the method 400.

Figure 5:
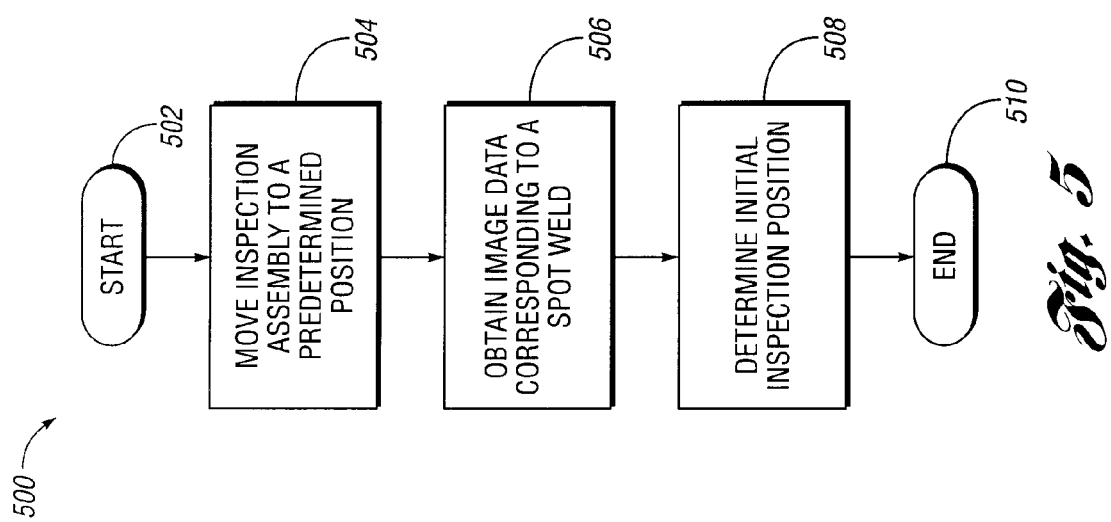
FIG. 5 is a flow diagram of a method for determining an initial inspection position using an artificial vision device according to an embodiment of the present invention.

Referring to FIG. 5, a flow diagram of a method 500 for determining an initial inspection position using an artificial vision device (e.g., 124) according to at least one embodiment of the present invention is shown. The method 500 may be advantageously implemented in connection with the system 100, described previously in connection with FIGS. 1 and 2, the method 400 described previously in connection with FIG. 4, and/or any appropriate system and/or method to meet the design criteria of a particular application. In particular the method 500 is generally performed by a logical device, such as the controller 130. The method 500 generally includes a plurality of blocks or steps that may be performed serially. As will be appreciated by one of ordinary skill in the art, the order of the blocks/steps shown in FIG. 5 are exemplary and the order of one or more block/step may be modified within the spirit and scope of the present invention. Additionally, the blocks/steps of the method 500 may be performed in at least one non-serial (or non-sequential) order, and one or more blocks/steps may be omitted to meet the design criteria of a particular application. Similarly, two or more of the blocks/steps of the method 500 may be performed in parallel. Step 502 generally represents an entry point into the method 500.

At step 504, an inspection assembly (e.g., 112) may be moved to a predetermined position. In general, the predetermined position is determined such that a spot weld (e.g., 102) on a workpiece (e.g., 104) is brought into view of an artificial vision device (e.g., 124) coupled to the inspection assembly. It should be understood that step 504 may be omitted in an embodiment wherein the artificial vision device is mounted external to the inspection assembly (i.e., position of the inspection assembly does not correspond to position of the artificial vision device). It should also be understood that the predetermined position may, in an embodiment, correspond to a home position and the step of moving the inspection assembly to a predetermined position may be performed prior to the presentation of a workpiece for inspection (e.g., at the completion of a preceding work cycle). From step 504, the method 500 may fall through to step 506.

At step 506, image data corresponding to the spot weld may be obtained using the artificial vision device. From step 506, the method 500 may fall through to step 508.

At step 508, the initial inspection position may be determined via a controller and/or other logical device based at least in part on the image data. In at least one embodiment, the initial inspection position corresponds to the center of a weld spot and the initial inspection position is determined within 0.1 millimeters of the center. From step 508, the method 500 may fall through to step 510.

Step 510 generally represents an exit point out of the method 500.

Accordingly, an artificial vision device may provide increased accuracy when determining the initial inspection position.

Figure 6A:
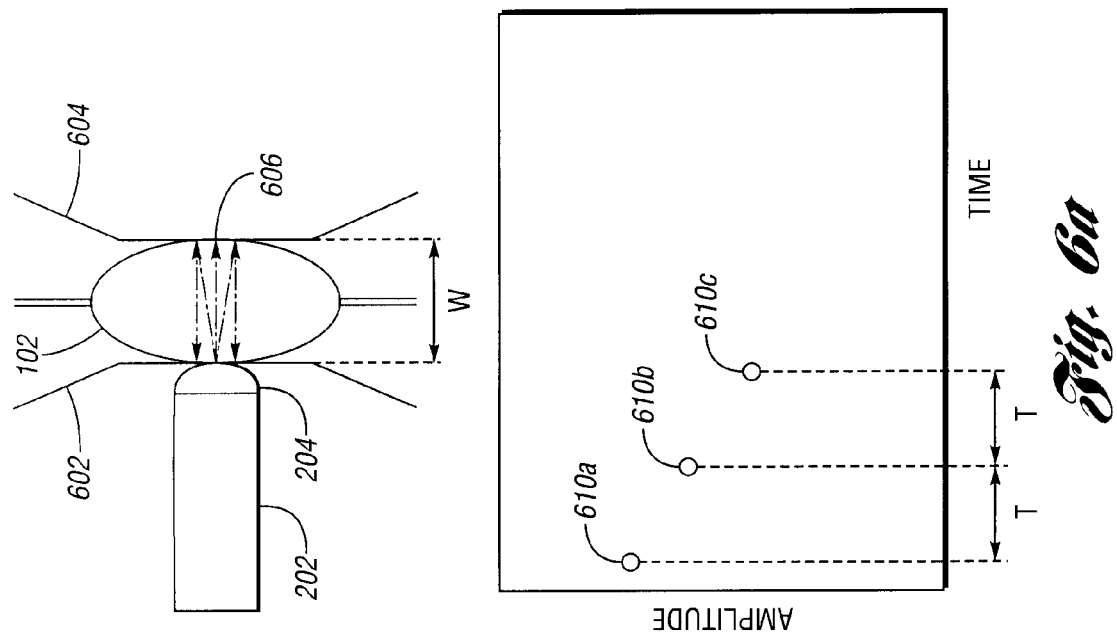
FIGS. 6(a-c) are diagrams of spot welds and corresponding simulated spot weld echo state plots.

Referring to FIG. 6a, a diagram is provided of a good (i.e., desirable, to specification, etc.) spot weld 102 between a first 602 and second 604 surface, and a corresponding simulated spot weld echo state. As illustrated, the width of the spot weld 102 (i.e., W) generally corresponds to (e.g., may be proportional to) an amount of time (T) required for an ultrasound wave generated by the ultrasound device 202 to be reflected off of a back surface 606 of the spot weld 102 and received, as an echo wave, at the ultrasound device 202. Accordingly, the time delay (T) between adjacent echo waves (e.g., 610a & 610b, and 610b & 610c) is generally related to the width (W) of the spot weld 102.

Figure 6B:
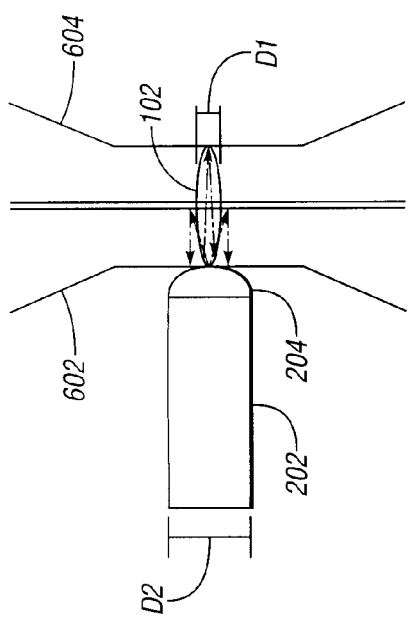
Figure 6B:
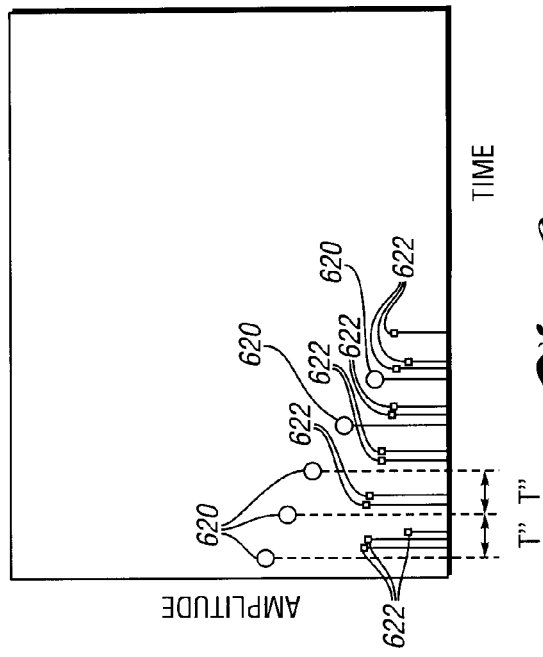

Referring to FIG. 6b, a diagram is provided of an omitted (i.e., missing) spot weld between the first 602 and second 604 surfaces, and a corresponding simulated spot weld echo state. As illustrated, the width of the first surface 602 (i.e., W') generally corresponds to (e.g., may be proportional to) an amount of time (T') required for an ultrasound wave generated by the ultrasound device 202 to be reflected off of a back surface 608 of the first surface 602 and received, as an echo wave, at the ultrasound device 202. Accordingly, the time delay (T') between adjacent echo waves (e.g., 610d & 610e, and 610e & 610f) is generally proportional to the width (W') of the first surface 602. Accordingly, an omitted spot weld may be indicated by a time delay corresponding to T' and a good spot weld may be indicated by a time delay corresponding to T. In general, the time delay corresponding to a good spot weld (i.e., T) is greater than the time delay corresponding to an omitted (i.e., missing) spot weld (i.e., T') because the ultrasound wave must travel farther before being reflected as an echo wave.

Figure 6C:
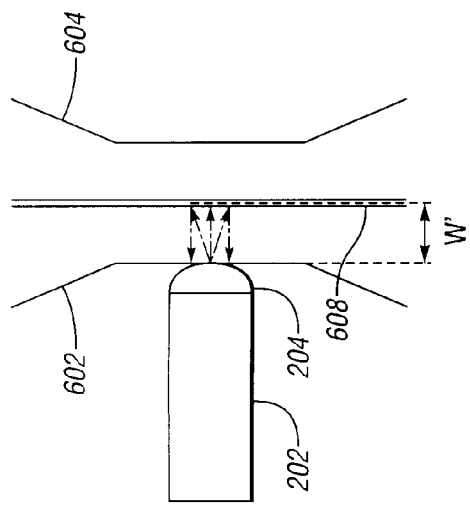
Figure 6C:
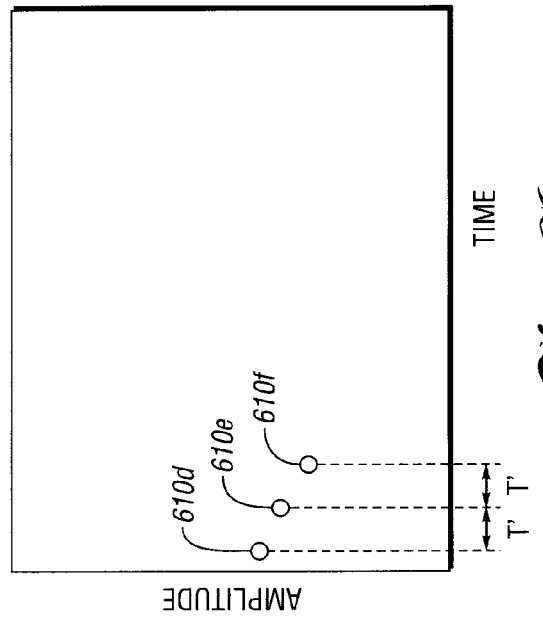

Referring to FIG. 6c, a diagram is provided of a spot weld 102 between first 602 and second 604 surfaces having a diameter (i.e., D1) less than the diameter (i.e., D2) of the ultrasound device 202. As illustrated in the corresponding simulated spot weld echo state, primary echo waves 620 corresponding to the welded portion (i.e., spot weld 102) of the first 602 and second 604 surfaces are generally intermixed with secondary echo waves 622 corresponding to non-welded portions of the first 602 and second 604 surfaces. As such, the diameter (D1) of the spot weld 102 may be determine with reference to the diameter (D2) of the ultrasound device 202.

Accordingly, in at least one embodiment, a spot weld echo state corresponding to a particular spot weld 102 may be inspected by reference to one or more echo states representing various known spot weld 102 configurations.

In accordance with various embodiments of the present invention, the methods described herein may operate as software running on one or more controllers having one or more processors. Dedicated hardware implementations including, but not limited to, application specific integrated circuits, programmable logic arrays, electro-mechanical relays, and/or other hardware devices can likewise be constructed to implement the methods described herein.

It should also be noted that the software implementations of the present invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored.

As is clear, then, from the above disclosure and subsequent claims, one or more embodiments of the present invention may provide any of a number of benefits such as decreasing the amount of time required to inspect a spot weld such that on-line inspection and/or an increase in the inspection rate may be provided. In addition, one or more embodiments of the present invention may reduce the risk of damaging the spot weld and/or part during inspection.

While the best mode for carrying out the invention has been described in detail, those familiar with the art to which this invention relates will recognize various alternative designs and embodiments for practicing the invention as defined by the following claims.

What is claimed:

1. A system for inspecting a spot weld on a workpiece, the system comprising:
an actuator;
an inspection assembly coupled to the actuator and comprising an ultrasound device and one or more adjustment motors coupled to the ultrasound device, wherein the ultrasound device is configured to generate one or more ultrasound waves and receive one or more echo waves; and
a controller electronically coupled to the inspection assembly and configured to identify a spot weld echo state based at least in part on the one or more echo waves, and determine whether the spot weld echo state corresponds to a member of a set of predetermined echo states;
wherein the actuator is configured to position the inspection assembly at an initial inspection position, and the one or more adjustment motors are configured to manipulate the ultrasound device when the spot weld echo state does not correspond to a member of the set of predetermined echo states such that a first end of the ultrasound device disposed adjacent to the workpiece is held substantially stationary and a second end of the ultrasound device disposed opposite the first end is moved along a curved path.

2. The system of claim 1 wherein the controller is further configured to generate an accept signal or a reject signal based at least in part on the spot weld echo state when the spot weld echo state corresponds to a member of the set of predetermined echo states.

3. The system of claim 1 wherein the workpiece is coupled to a workpiece presenter and the workpiece presenter is coupled to a material handling system.

4. The system of claim 3 wherein the actuator is further configured to move the inspection assembly during inspection of the spot weld such that a relative position between the inspection assembly and the spot weld is substantially constant while the workpiece presenter moves along the material handling system.

5. The system of claim 1 wherein the inspection assembly further comprises an electronic vision device configured to obtain image data corresponding to the spot weld, and the initial inspection position is determined based at least in part on the image data.

6. The system of claim 1 wherein at least part of the curved path includes a spiral.

7. A method for inspecting a spot weld on a workpiece, the method comprising the steps of:
moving an inspection assembly comprising an ultrasound device to an initial inspection position proximate the spot weld;
generating one or more ultrasound waves using the ultrasound device;
receiving one or more echo waves using the ultrasound device;
identifying, using a controller, a spot weld echo state based at least in part on the one or more echo waves;
determining whether the spot weld echo state corresponds to a member of a set of predetermined echo states; and
manipulating the ultrasound device when the spot weld echo state does not correspond to a member of the set of predetermined echo states such that a first end of the ultrasound device disposed adjacent to the workpiece is held substantially stationary and a second end of the ultrasound device disposed opposite the first end is moved along a curved path.

8. The method of claim 7 further comprising the step of generating an accept signal or a reject signal based at least in part on the spot weld echo state when the spot weld echo state corresponds to a member of the set of predetermined echo states.

9. The method of claim 7 wherein the ultrasound device is disposed substantially perpendicular to the spot weld and substantially centered on the spot weld when the inspection assembly is at the initial inspection position.

10. The method of claim 7 further comprising the step of determining whether to abort inspection of the spot weld when the spot weld echo state does not correspond to a member of the set of predetermined echo states.

11. The method of claim 7 wherein the curved path is substantially defined by a spiral such that an increasing angle is formed between the ultrasound device and an axis passing through the first and second ends prior to the manipulation.

12. The method of claim 11 wherein the increasing angle has a maximum value of 10 degrees.

13. The method of claim 7 further comprising repeating the generating, receiving, identifying and determining steps while the ultrasound device is manipulated.

14. The method of claim 7 wherein the inspection assembly further comprises an artificial vision device and the method further comprises the steps of:
moving the inspection assembly to a predetermined position;
obtaining image data corresponding to the spot weld using the artificial vision device; and
determining via a controller the initial inspection position based at least in part on the image data.

15. The method of claim 7 further comprising the step of generating a report using a controller, wherein the report is based at least in part on the spot weld echo state of one or more spot welds.

16. A system for inspecting a spot weld on a workpiece, the system comprising:
an actuator;
an inspection assembly coupled to the actuator and comprising an ultrasound device and one or more adjustment motors coupled to the ultrasound device; and
one or more controllers electronically coupled to at least one of the actuator and the inspection assembly, the one or more controllers configured to perform the steps of:
moving the ultrasound device via at least one of the actuator and the one or more adjustment motors to an initial inspection position proximate the spot weld;
generating one or more ultrasound waves via the ultrasound device;
receiving one or more echo waves via the ultrasound device;

identifying a spot weld echo state based at least in part on the one or more echo waves;

determining whether the spot weld echo state corresponds to a member of a set of predetermined echo states;

manipulating the ultrasound device via the one or more adjustment motors when the spot weld echo state does not correspond to a member of the set of predetermined echo states such that a first end of the ultrasound device disposed adjacent to the workpiece is held substantially stationary and a second end of the ultrasound device disposed opposite the first end is moved along a curved path, at least part of the curved path including a spiral; and generating an accept signal or a reject signal based at least in part on the spot weld echo state when the spot weld echo state corresponds to a member of the set of predetermined echo states.

17. The system of claim 16 wherein the second end is moved along the curved path when the first end is not positioned in alignment with the spot weld.

18. The system of claim 16 further comprising an artificial vision device configured to obtain image data corresponding to the spot weld, wherein the initial inspection position is determined based at least in part on the image data.

19. The system of claim 16 wherein the ultrasound device includes a rubber tip for coupling the ultrasound device to the spot weld.

20. The system of claim 16 wherein a member of the one or more controllers is electronically coupled to a network.

* * * * *